US00PP09248P

United States Patent [19]

Egger

[11] Patent Number: Plant 9,248

[45] Date of Patent: Aug. 15, 1995

[54] *LONGIFLORUM*×ASIATIC HYBRID LILY PLANT NAMED 'CEB WINE'

[75] Inventor: Donald L. Egger, Aurora, Oreg.

[73] Assignee: Cebeco Lillies, Inc., Aurora, Oreg.

[21] Appl. No.: 333,494

[22] Filed: Nov. 2, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist Sparkman Campbell Leigh & Whinston

[57] ABSTRACT

A new and distinct lily hybrid named 'Ceb Wine' characterized by upright, large rose colored flowers with thick petals on tall, strong stems excellent for cut flower production.

1 Drawing Sheet

BACKGROUND OF THE INVENTION

The present invention comprises a new and distinct cultivar of lily hybrid, referred to commercially as a *longiflorum*-Asiatic Lily Hybrid, referred to by the cultivar name 'Ceb Wine'.

This invention is the product of a controlled breeding program in Aurora, Ore. The seed parent was an unnamed seedling identified as 79-186. This seed parent has not been released and was kept proprietary. The pollen parent was PAM #2, another proprietary non-released plant.

The *longiflorum*-Asiatic cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages, not necessarily in combination, over an Asiatic lily: (1) often larger flowers; (2) often larger, waxier leaves; (3) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions. This phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) large, upright, clear rose pink flowers with a small, creamy white center; (2) thick tepals which strongly overlap; (3) large pink buds; (4) tall, strong stems; (5) scorch resistance; and (6) early bloom time. Bulbs of this plant may be precooled and forced out of season for very uniform cut flower production.

To the inventor's knowledge, there are no other *longiflorum*-Asiatic lily hybrids with this color flower suitable for cut flower forcing on the market.

Asexual reproduction of this new variety has been initially and subsequently accomplished at Cebeco Lillies, Inc. in Aurora, Ore., by scaling and tissue culture. The resulting plants have shown that the above-mentioned unique features are stable and reproduce true to type in each successive propagation.

Figure 2:
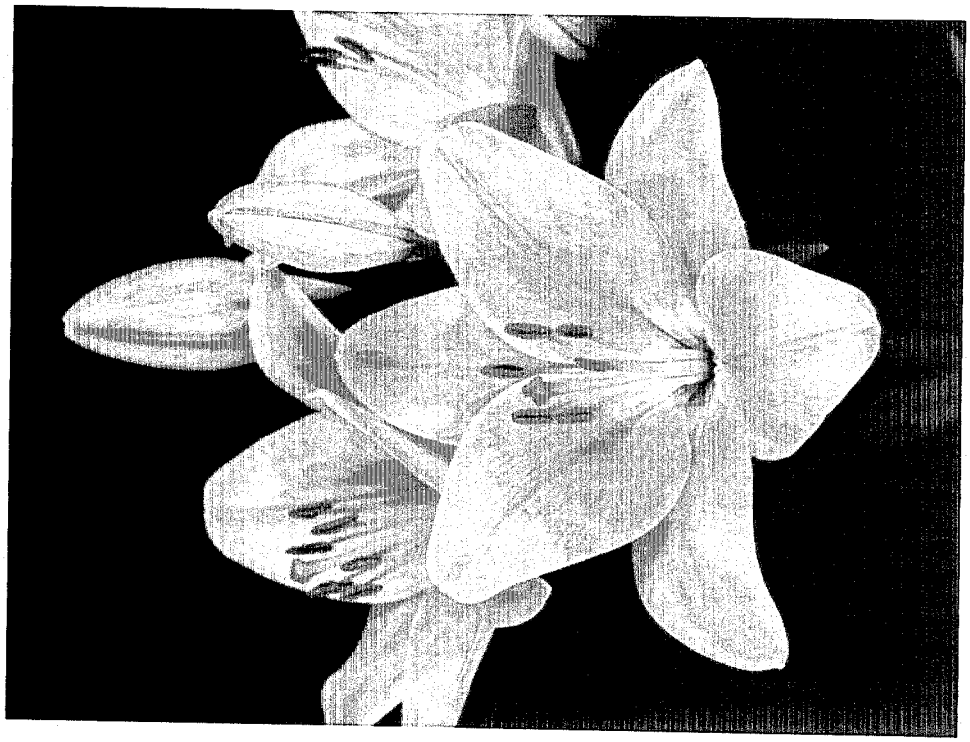
FIG. 2 is a close-up photograph which illustrates in greater detail a single flower of the new plant.
Figure 1:
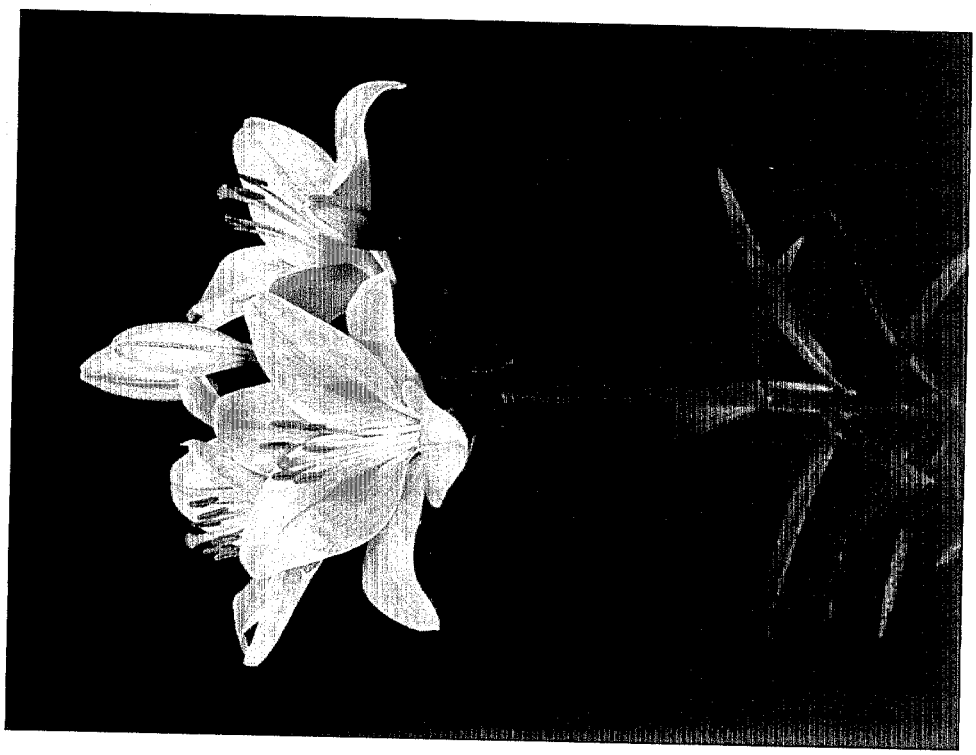
FIG. 1 is a photograph showing the 'Ceb Wine' lily.

The photographs of the drawing were taken in August 1993 in a studio and illustrate the typical flower and foliage form, with color being as true as is reasonably possible in this type of color photograph.

DETAILED DESCRIPTION

The following is a detailed description of the invention based on plants produced under commercial practices in the Cebeco Lilies, Inc. greenhouses in Aurora, Ore. in July 1993. Color references are made to the Royal Horticultural Society Colour Chart (RHS), except where the context indicates a term having its ordinary dictionary meaning.

THE PLANT

Origin: Seedling.

Parentage:

- *Seed parent.*—79-186.
- *Pollen parent.*—PAM #2.

Commercial classification: Upright *longiflorum*-Asiatic hybrid, cut flower type.

Classification: Division VIII, according to the Horticultural Classification of Lilies by The Royal Horitcultural Society of London.

Form: Single erect stem bearing terminal cluster of flowers.

Height: About 86 cm. from the top of the soil to the top of the flowers from bulbs of 14 cm. in circumference.

Growth habit: Vigorous, upright and rigid.

Foliage:

- *Arrangement.*—Spiral.
- *Quantity.*—Average.
- *Leaf size.*—Variable to about 7.5 cm. long and about 1.2 cm. wide.
- *Leaf shape.*—Linear to lanceolate with soft hairs on the leaf margins and base.
- *Texture.*—Leathery.
- *Aspect.*—Matte.
- *Color.*—Medium green, closest to 147A on both sides.

Bulbs:

- *Size.*—Variable, ranging to about 12–14 cm. in circumference as used commercially.
- *Color.*—White.

THE BUD

Size: To about 8 cm. long and 2 cm. wide just prior to opening.

Shape: Ovoid and covered sparsely with soft white hairs.

Rate of opening: The mature bud opens slowly in response to light.

Color: Rose pink (Yellow green heavily blushed with Grayed-Purple Group 185C).

THE FLOWER

Blooming habit: Annually, once and early season.

Days to bloom: Flowers approximately 75 days after spring greenhouse planting under typical commercial flower forcing conditions of 15° Celsius night time temperatures.

Inflorescence size: About 16 cm. high and 22 cm. wide when there are five flowers present.

Flower size: Medium large.

*Diameter.*—About 13 cm.

*Depth.*—About 8 cm.

Borne: In an umbel or modified raceme of 5 to 10 flowers from bulbs, 12–14 cm. in circumference.

Shape: When the flower first opens it is bowl-shaped. Later, the shape flattens out and the tepals reflex at the tips.

Tepalage:

*Number.*—Six.

*Arrangement.*—Imbricated.

*Shape.*—Ovate.

*Texture.*—Leathery, thicker than average.

*Aspect.*—Satiny.

*Size.*—Length: About 9 cm. Width: Inner tepals — about 4.2 cm. Outer tepals — about 3.8 cm. Depth of imbrication: About 2 cm.

*Nectary.*—About 2.5 cm. long; the bottom half is yellow green in color and the top half is the tepal color; pubescent.

*Projections.*—None.

*Spots.*—None.

*Blush.*—None.

*Color.*—Topside: Rose pink. Between Red Group 54A and Red-Purple Group 58A. Topside Base: Creamy white. White Group 155A. Bottomside: Dull Rose Pink. Grayed-Purple Group 185D.

*Discoloration.*—Slightly duller color with age.

*Fragrance.*—Slight.

*Lasting quality.*—Good.

Pedicel:

*Length.*—Usually about 5–11 cm.

*Color.*—Yellow-green faintly mottled red purple and sparsely covered with short soft white hairs.

*Orientation.*—Some pedicels may be completely vertical, others ascending upwardly from about 45° from the horizontal.

THE REPRODUCTIVE ORGANS

Stamens:

*Number.*—Six, typical of the genus Lilium.

*Anthers before dehiscence.*—Size: About 17 mm. Color: Closest to Yellow-Orange Group 22A, but a little more brown.

*Filaments.*—Length: About 62 mm. Color: Rose. Red-Purple Group 58A at the top to white at the base.

*Pollen.*—Color: Brown. Grayed-Orange Group 166B.

Pistil:

*Number.*—One.

*Style.*—Length: About 52 mm. Color: Grayed-Yellow Group 162C lightly blushed with Grayed-Purple Group 187B.

*Stigma.*—Color: Grayed-Purple Group 187B.

THE FRUIT

Fertility: The fruit is infertile.

Shape: Ovoid.

Color at maturity: Soft Brown.

I claim:

1. A new and distinct cultivar of *longiflorum*-Asiatic hybrid lily plant substantially as herein shown and described.

* * * * *